US012765854B2

(12) United States Patent
Ito et al.

(10) Patent No.: US 12,765,854 B2
(45) Date of Patent: Oct. 20, 2026

(54) RE-IMAGING DETERMINATION SUPPORT DEVICE, LEARNING DEVICE, RE-IMAGING SUPPORT DEVICE, RECORDING MEDIUM, AND RE-IMAGING DETERMINATION SUPPORT METHOD

(71) Applicant: Konica Minolta, Inc., Tokyo (JP)

(72) Inventors: Ryohei Ito, Hino (JP); Amai Shimizu, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 897 days.

(21) Appl. No.: 18/167,668

(22) Filed: Feb. 10, 2023

(65) Prior Publication Data

US 2023/0263494 A1 Aug. 24, 2023

(30) Foreign Application Priority Data

Feb. 18, 2022 (JP) ................................ 2022-023404

(51) Int. Cl.
*A61B 6/00* (2024.01)

(52) U.S. Cl.
CPC ........ *A61B 6/5211* (2013.01); *G06T 2207/10* (2013.01)

(58) Field of Classification Search
CPC ......... G06T 2207/10116; G06T 7/0012; G06T 2207/30008; G06T 2207/10081; A61B 6/463; A61B 6/465; A61B 6/542; A61B 6/54; A61B 6/032
See application file for complete search history.

(56) References Cited

U.S. PATENT DOCUMENTS

2022/0028075 A1* 1/2022 Sugahara ................. A61B 6/54
2022/0151573 A1* 5/2022 Sugahara ............. A61B 6/5229

FOREIGN PATENT DOCUMENTS

JP 2019-33830 A 3/2019
JP 2021-097864 A 7/2021

OTHER PUBLICATIONS

Notice of Reasons for Refusal, mailed on Jul. 15, 2025, which was issued for the corresponding Japanese Patent Application No. 2024-216133, 7 pages, with English translation.
Notice of Reasons for Refusal, mailed on Aug. 27, 2024, issued for the corresponding Japanese Patent Application No. 2022-023404, with English Translation.

* cited by examiner

*Primary Examiner* — Raphael Schwartz
(74) *Attorney, Agent, or Firm* — LUCAS & MERCANTI, LLP

(57) ABSTRACT

A re-imaging determination support device including a hardware processor that: judges a first misalignment of a predetermined region in a radiographic image; judges a second misalignment of a predetermined region in the radiographic image; and outputs re-imaging determination support information that supports determining whether or not to perform re-imaging for the radiographic image, based on at least a judgement of the first misalignment and a judgement of the second misalignment.

25 Claims, 7 Drawing Sheets

RE-IMAGING DETERMINATION SUPPORT DEVICE, LEARNING DEVICE, RE-IMAGING SUPPORT DEVICE, RECORDING MEDIUM, AND RE-IMAGING DETERMINATION SUPPORT METHOD

REFERENCE TO RELATED APPLICATIONS

The entire disclosure of Japanese Patent Application No. 2022-023404 filed on Feb. 18, 2022 is incorporated herein by reference in its entirety.

TECHNICAL FIELD

The present invention relates to a re-imaging determination support device, a learning device, a re-imaging support device, a recording medium, and a re-imaging determination support method.

DESCRIPTION OF THE RELATED ART

In recent years, optimization of medical exposure and dose control have been of particular importance, and there is a need to reduce radiation dose in imaging with radiographic imaging devices. In order to avoid unnecessary radiation exposure, it is necessary to devise ways to minimize re-imaging.

In radiographic imaging, if the patient's imaging posture is not appropriate, misalignment occurs in the patient's positioning during imaging, and re-imaging is necessary. Although there are known techniques to determine whether or not to perform re-imaging by judging the misalignment of patient positioning, more accurate judgement of the positioning misalignment is desired in order to avoid re-imaging performed multiple times.

Conventional techniques for judging the positioning misalignment at joints are known as the techniques for judging the misalignment of patient positioning (see, for example, JP 2021-097864 A).

SUMMARY OF THE INVENTION

In the knee, for example, when imaging in the supine position, the joint has less freedom. Positioning on the femoral side is difficult and hard to change. Therefore, conventionally, the misalignment of positioning at the knee has been judged by determining the misalignment of positioning of one region on the lower leg side. Similarly, in the ankle, for example, when imaging in the supine position, the joint has less degrees of freedom. Positioning on the lower leg side is difficult and hard to change. Therefore, the misalignment of positioning at the ankle has conventionally been judged by determining the misalignment of positioning of one region on the toe side.

On the other hand, because the elbow has a high degree of freedom of the joint, the positioning misalignment is likely to occur in both directions (forearm side and upper arm side) in judging the positioning misalignment at the elbow. Therefore, judging the positioning misalignment in only one direction (forearm side or upper arm side) by judging the positioning misalignment in only one region as in the conventional method, does not provide highly accurate judgement of elbow positioning misalignment.

Also, in the knee and ankle, although the degree of freedom of the joint is low, there is a possibility of misalignment in positioning in both directions (for example, thigh side and lower leg side for the knee, or lower leg side and toe side for the ankle). Therefore, in determining the misalignment of positioning of joints, including the knee and ankle, if only the misalignment of positioning in one direction is determined by determining the misalignment of positioning in only one region, the misalignment cannot be judged with a high degree of accuracy.

An object of the present invention is to judge the misalignment of joint positioning with high accuracy.

To achieve at least one of the abovementioned objects, according to an aspect of the present invention, there is provided a re-imaging determination support device comprising a hardware processor that: judges a first misalignment of a predetermined region in a radiographic image; judges a second misalignment of a predetermined region in the radiographic image; and outputs re-imaging determination support information that supports determining whether or not to perform re-imaging for the radiographic image, based on at least a judgement of the first misalignment and a judgement of the second misalignment.

To achieve at least one of the abovementioned objects, according to another aspect of the present invention, there is provided a learning device that learns with at least a radiographic image, information about a first misalignment of a predetermined region in the radiographic image, and information about a second misalignment of a predetermined region in the radiographic image, as teacher data.

To achieve at least one of the abovementioned objects, according to another aspect of the present invention, there is provided a re-imaging determination support device including: a learned model in which at least a radiographic image, information about a first misalignment of a predetermined region in the radiographic image, and information about a second misalignment of a predetermined region in the radiographic image are learned as teacher data; an obtainer that obtains a radiographic image; and a hardware processor that outputs re-imaging determination support information that supports determining whether or not to perform re-imaging for the radiographic image, based on the learned model and the radiographic image obtained by the obtainer.

To achieve at least one of the abovementioned objects, according to another aspect of the present invention, there is provided a re-imaging support device comprising a hardware processor that: judges a first misalignment of a predetermined region in a radiographic image; judges a second misalignment of a predetermined region in the radiographic image; and outputs re-imaging support information that supports re-imaging for the radiographic image, based on at least a judgement of the first misalignment and a judgement of the second misalignment.

To achieve at least one of the abovementioned objects, according to another aspect of the present invention, there is provided a non-transitory recording medium storing a computer-readable program, the program causing a computer to perform: first judging that is judging a first misalignment of a predetermined region from a radiographic image; second judging that is judging a second misalignment of a predetermined region in the radiographic image; and outputting that is outputting re-imaging determination support information that supports determining whether or not to perform re-imaging for the radiographic image, based on at least a judgement of the first misalignment and a judgement of the second misalignment.

To achieve at least one of the abovementioned objects, according to another aspect of the present invention, there is provided a re-imaging determination support method including: first judging that is judging a first misalignment of a predetermined region in a radiographic image; second judging that is judging a second misalignment of a predetermined region in the radiographic image; and outputting that is outputting re-imaging determination support information that supports determining whether or not to perform re-imaging for the radiographic image, based on at least a judgement of the first misalignment and a judgement of the second misalignment.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein.

DETAILED DESCRIPTION

The embodiment of the present invention will be described below with reference to the drawings. However, the scope of the present invention is not limited to the following embodiments and illustrated examples.

<1. Radiographic Imaging System>

First, the schematic configuration of the radiographic imaging system for the embodiment (hereinafter referred to as the system 100) is described.

Figure 1:
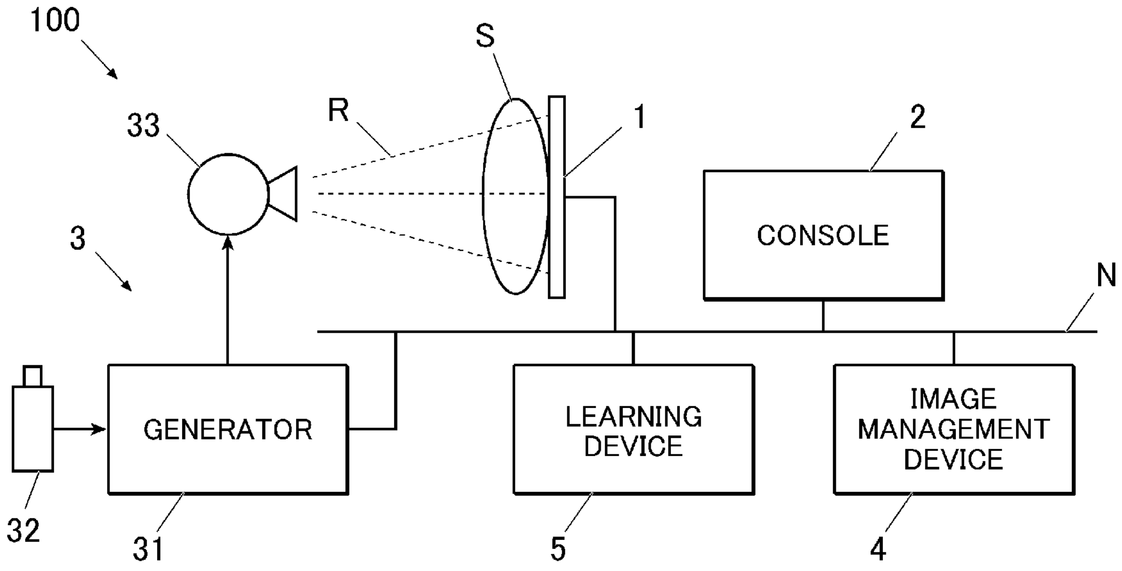
FIG. 1 is a block diagram showing an example of a radiographic imaging system for an embodiment of the present invention.

FIG. 1 is a block diagram showing the system 100.

The system 100 has a radiographic image imaging device (hereinafter, referred to as an the imaging device 1) and a the console 2, as shown in FIG. 1.

The system 100 for the embodiment further includes a radiation generating device (hereinafter, referred to as a generating device 3), an the image management device 4, and a the learning device 5.

The devices 1-5 can communicate with each other via a communication network N (LAN (Local Area Network), WAN (Wide Area Network), Internet, and the like), for example.

The system 100 may be installed in an imaging room, or it may be configured to be mobile (for example, in a mobile vehicle).

The system 100 may also be able to communicate with a Hospital Information System (HIS), Radiology Information System (RIS), and the like, which are not shown in the figure.

[1-1. Radiation Generating Device]

The generating device 3 has a generator 31, an irradiation instruction switch 32, and a radiation source 33.

The generator 31 applies a voltage to the radiation source 33 (tube) according to preset imaging conditions based on the operation of irradiation instruction switch 32.

When the voltage is applied from the generator 31, the radiation source 33 is designed to generate a dose of radiation R (such as X-rays) in proportion to the applied voltage.

The generating device 3 for the embodiment is designed to generate radiation R in a manner that is appropriate to the form of the radiographic image to be generated (still image, dynamic image with multiple frames).

In the case of still images, radiation R is irradiated only once per each press of the irradiation instruction switch 32.

In the case of dynamic image, irradiation of pulsed radiation R is repeated multiple times per predetermined time (for example, 15 times per second) per pressing of the irradiation instruction switch 32, or irradiation of radiation R is continued for a predetermined time.

[1-2. Radiographic Image Imaging Device]

The imaging device 1 produces digital data of a radiographic image of the imaging part of the subject.

The imaging device 1 for the embodiment is a portable FPD (Flat Panel Detector).

Specifically, though not shown in the figure, the imaging device 1 for the embodiment includes: the sensor substrate that is a two-dimensional (matrix) array of imaging elements that generate a charge in accordance with the dose when exposed to radiation R and switch elements that accumulate and release the charge; the scanning section that switches each switch element on and off; the readout section that reads out the amount of charge emitted from each pixel as a signal value; the controller that controls each part and generates a radiographic image from multiple signal values read by the readout section; the communication unit that transmits the generated radiographic image data, various signals, and the like to other devices (the console 2, generating device 3, the image management device 4, and the like) and receives various information and various signals from other devices; and the like.

The imaging device 1 is designed to generate image data of still images (hereinafter, still image data) or dynamic image (hereinafter, dynamic image data) by accumulating and releasing electric charges and reading out signal values in synchronization with the timing when radiation R is irradiated from the generating device 3.

When generating the still image data, the radiographic image is generated only once per each press of the irradiation instruction switch 32.

When generating the dynamic image data, the generation of frames constituting the dynamic image is repeated multiple times per predetermined time (for example, 15 times per second) for each press of the irradiation instruction switch 32.

The imaging device 1 may be integrated with the generating device 3.

[1-3. Console]

The console 2 sets various imaging conditions for at least one of the imaging device 1 and the generating device 3.

The console 2 consists of a PC, dedicated device, and the like

Imaging conditions include, for example, conditions related to the subject S (the imaging part, the imaging direction, body size, and the like), conditions related to irradiation of radiation R (tube voltage and tube current, irradiation time, current time product (mAs value), and the like), and conditions related to image reading by the imaging device 1.

The console 2 may automatically set imaging conditions based on test order information obtained from other systems (HIS, RIS, and the like) or based on operations made by the user (for example, technician) on the operation interface 25 (manually)

The console 2 for the embodiment also serves as a re-imaging determination support device and a re-imaging support device.

In other words, the console 2 functions as a re-imaging determination support device that outputs re-imaging determination support information to assist the user in determining whether or not to perform re-imaging for the radiographic image generated by the imaging device 1, at the time of the determination to re-image (timing when the user has not yet determined whether or not to re-image the radiographic image). The console 2 also functions as a re-imaging support device that outputs re-imaging support information that supports the re-imaging of the radiographic image generated by the imaging device 1 at the timing when re-imaging is performed (timing when the determination to re-imaging has already been made).

[1-4. Image Management Device]

The image management device 4 manages the image data generated by the imaging device 1.

The image management device 4 is Picture Archiving and Communication System (PACS), diagnostic imaging workstation (IWS), and the like.

[1-5. Learning Device]

The learning device 5 is a device that learns a plurality of pieces of teacher data to generate a learned model M to be used in the console 2 to perform the re-imaging determination support information generation process described below.

The learning device 5 is composed of, for example, a CPU (Central Processing Unit), a storage, a communication unit, an operation interface, a display, and the like. The generation of the learned model M based on the teacher data is realized by the cooperation of the CPU and a program stored in the storage.

The learning device 5, for example, generates multiple types of learned models M according to the imaging part and the imaging direction.

In the embodiment, the learning device 5 performs machine learning with, as teacher data, a set of the radiographic image of a joint as the imaging part (for example, the joint of elbow, knee, ankle, and the like), information about the first misalignment of a predetermined region of the radiographic image, and information about the second misalignment of a predetermined region of the radiographic image, and generates the learned model M (learned model M which estimates (decides) the information about the first misalignment and the information about the second misalignment of the predetermined region from the input radiographic image). Machine learning methods are not limited, but deep learning, for example, can be used.

The misalignment in the present invention refers to a deviation from the reference correct position or state. The reference correct position or state is, for example, the position or state in ideal positioning, which is considered optimal for diagnosis. For example, in a radiographic image of the side of the elbow joint, in ideal positioning, the humeral trochlea outer edge 71 and humeral capitulum edge 72 (see FIG. 2) almost overlap (coincide). In a radiographic image where the humeral trochlea outer edge 71 and humeral capitulum edge 72 do not overlap, a misalignment has occurred.

The predetermined region in the present invention is a region subject to judging the misalignment (first misalignment, second misalignment) in a radiographic image and is decided based on the imaging part information. This region is called the misalignment region in the embodiment. The predefined region subject to the judgement of the first misalignment is called the first misalignment region, and the predefined region subject to the judgement of the second misalignment is called the second misalignment region.

The first misalignment region and the second misalignment region are in the same joint region. The same joint region includes, for example, the same elbow joint region. It also includes the same ankle joint region, the same knee joint region, and so on. For example, the first misalignment region in the radiographic image of the side of the elbow joint is the inner elbow region bounded by the humeral trochlea outer edge 71 and the humeral capitulum edge 72 in the elbow joint (region shown with low-density dots in FIG. 2), and the second misalignment region is the outer elbow region bounded by the humeral trochlea outer edge 71 and humeral capitulum edge 72 in the same elbow joint as the first misalignment region (region shown with high-density dots in FIG. 2).

The first misalignment in the present invention is, for example, a misalignment in a first direction, and the second misalignment is, for example, a misalignment in a second direction different from the first direction. For example, the first misalignment in a predetermined region in a radiographic image of the side of the elbow joint includes the misalignment in the forearm direction of the humeral trochlea outer edge 71 and humeral capitulum edge 72 of the elbow joint region (shown in FIG. 7 with the sign 241*k*), and the second misalignment is the misalignment (shown in FIG. 7 with the sign 241*j*) of the humeral trochlea outer edge 71 and humeral capitulum edge 72 of the elbow joint region in the upper arm direction.

An indicator for the first misalignment is, for example, a misalignment amount in the first direction, and an indicator for the second misalignment is, for example, a misalignment amount in the second direction.

The misalignment amount of the present invention refers to the amount by which the position of a given part deviates from the reference when the ideal positioning is used as the reference. The ideal positioning is achieved when the misalignment amount is 0. For example, the misalignment amount in the first direction for a predetermined region in a radiographic image of the side of the elbow joint is the amount by which the humeral trochlea outer edge 71 and the humeral capitulum edge 72 are misaligned in the forearm direction (indicated by the sign D1 in FIG. 2), and the misalignment amount in the second direction is the amount by which the humeral trochlea outer edge 71 and the humeral capitulum edge 72 are misaligned in the upper arm direction (indicated by the sign D2 in FIG. 2).

The generation of the learned model M on the learning device 5 is described below, using the case of a radiographic image of the side of the elbow joint as an input.

Figure 2:
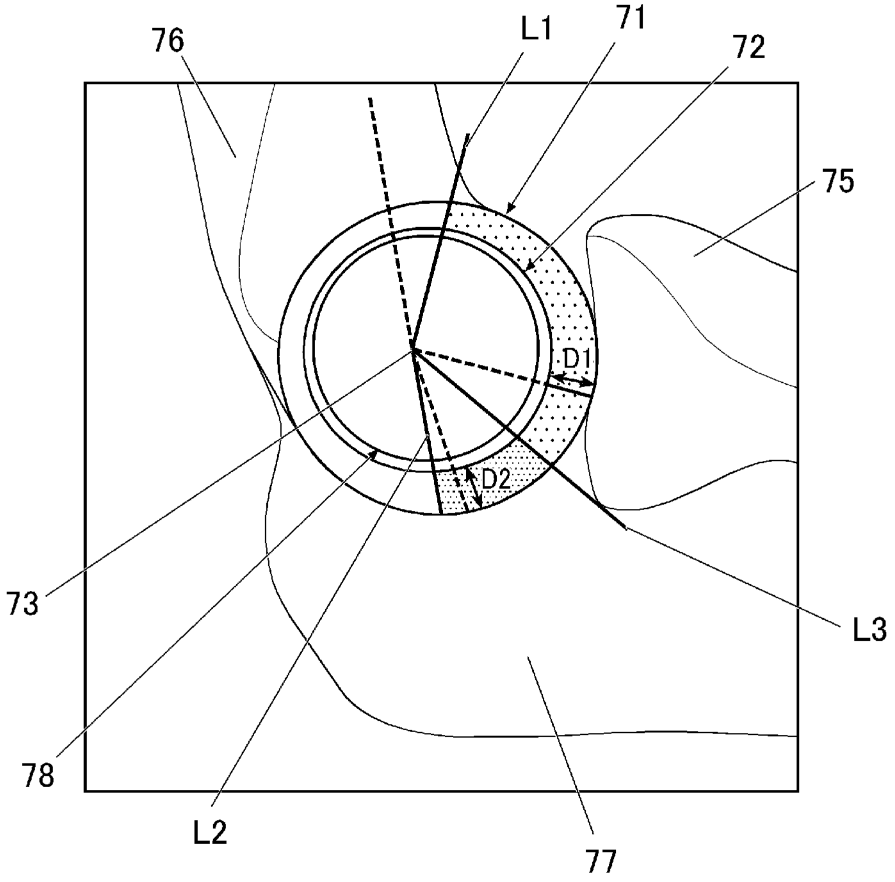
FIG. 2 shows schematically the side of the elbow joint.
Figure 3:
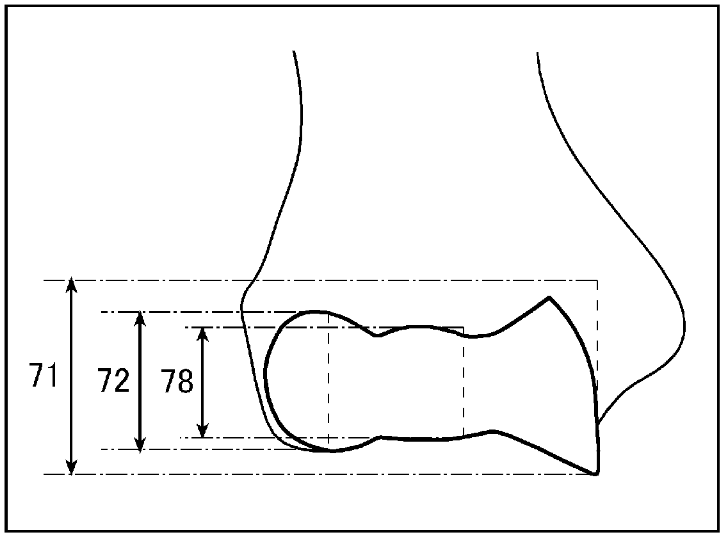
FIG. 3 shows schematically the front of the elbow joint.

FIG. 2 shows schematically the elbow joint side view. FIG. 3 shows schematically the frontal view of the elbow joint.

As described above, in the radiographic image of the side of the elbow joint, the ideal state of positioning is that the humeral trochlea outer edge 71 and humeral capitulum edge 72 are aligned. However, the humeral trochlea outer edge 71 and humeral capitulum edge 72 may not be aligned and may be misaligned in the forearm direction (forearm side) and/or the upper arm direction (upper arm side). In the embodiment, in the console 2, if the radiographic image is of the side of the elbow joint, this forearm misalignment of the humeral trochlea outer edge 71 and humeral capitulum edge 72 is the first misalignment, and misalignment of the humeral trochlea outer edge 71 and the humeral capitulum edge 72 in the upper arm direction as the second misalignment, the first and second misalignments are judged to generate re-imaging determination support information and re-imaging support information. The learning device 5 uses the imaged radiographic image as input to generate a learned model M for obtaining information about the first misalignment and information about the second misalignments for use in the console 2.

The learning device 5 takes one or more input data, including at least a radiographic image, and information about the misalignment of a predetermined region of the radiographic image (information about the first misalignment and information about the second misalignment) as output data, and the set of input and output data as teacher data to perform learning and generates a learned model M that estimates the output data when there is an input of input data for which the output data is unknown.

Figure 4A:
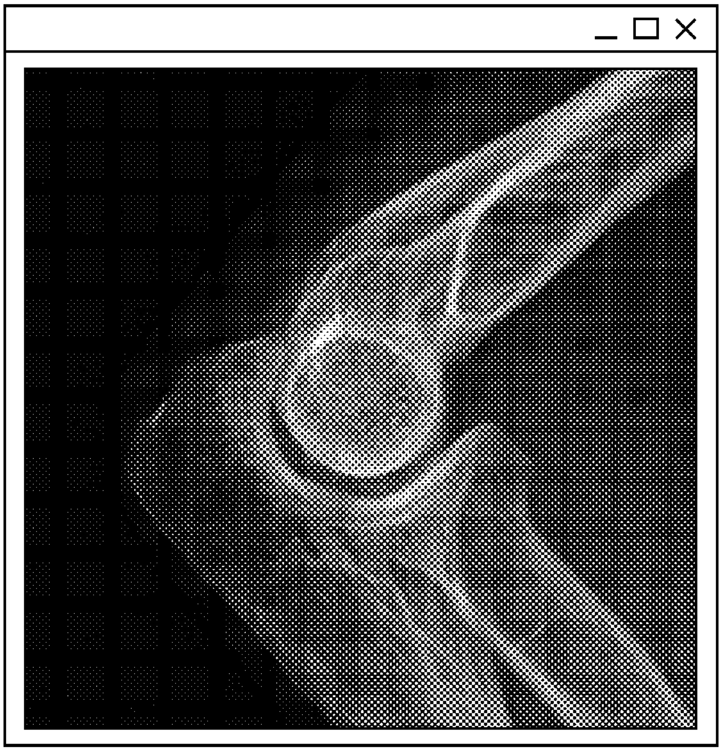
FIG. 4A shows an example of a radiographic image used as teacher data of input data.

In addition to the radiographic image shown in FIG. 4A, the input data in the teacher data may include, for example, the imaging part information (for example, whether the image is of the elbow joint), left/right information, imaging conditions such as dose during imaging, image information such as pixel size, and an image of the affected area learned with an optical camera. The more input data for the teacher data, the higher the estimation accuracy of the learned model M.

Figure 4B:
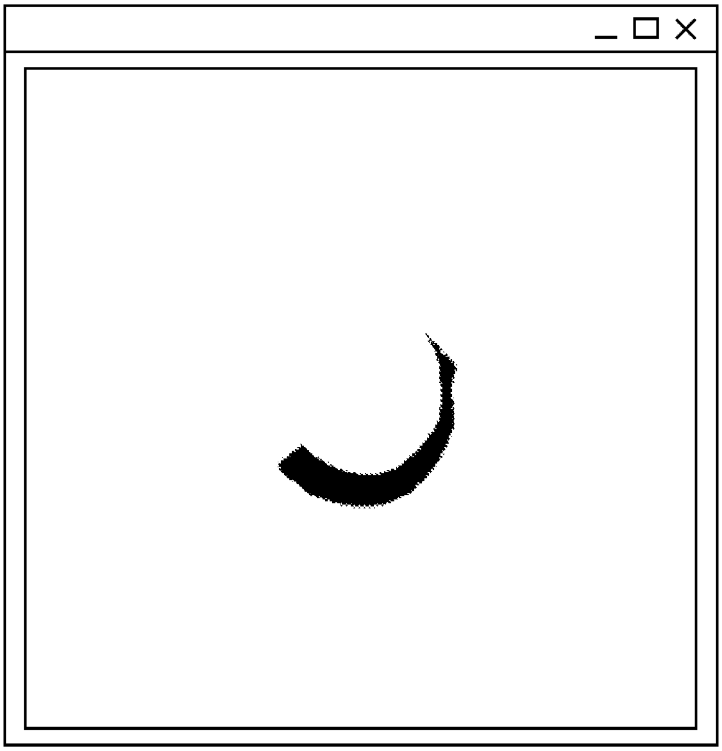
FIG. 4B shows an example of a region map used as teacher data of output data.

The output data in the teacher data includes, for example, for each of the first and second misalignments, the misalignment region map (coordinate information of misalignment region) shown in FIG. 4B, the misalignment amount, the information for changing the position of the part related to the misalignment (see below for details), information on the judgement rank for the degree of misalignment and whether there is an alert indicating that misalignment is occurring, and the coordinates of the trochlear axis (73 in FIG. 2) used to judge the misalignment. The misalignment region map may be a combined region of the first and second misalignment regions, in which case there is also required information separating the first and second misalignment regions (information on the line segment (for example, L3 in FIG. 2) separating both of the misalignment regions or information indicating to which of the first and second misalignment regions each coordinate in the misalignment region belongs, and the like). It may also include information such as whether the radiographic image has the target to be imaged (for example, whether it is an image of an elbow, whether a joint is captured, and the like). Furthermore, information indicating in which direction the irradiation center at the time of imaging is deviated from the ideal position may be included in the output data, so that information indicating in which direction the irradiation center at the time of imaging is deviated from the ideal position (certainty of position for each direction) may be output from the learned model M.

Misalignment region maps and other misalignment-related information to be used are decided by experts (radiologists and physicians) for the radiographic images.

In the embodiment, for example, when a radiographic image of the side of the elbow joint is inputted, the learning device 5 generates a learned model M that outputs the information of the first misalignment region (misalignment region map, information separating the first misalignment region and the second misalignment region) and the information of the second misalignment region (misalignment region map, information that separates the first misalignment region from the second misalignment region). This learned model M also outputs the coordinates of the trochlear axis 73.

Here, the range of the misalignment region (the combined region of the first and second misalignment regions) in the radiographic image of the side of the elbow joint is, for example, as shown in FIGS. 2 and 3, bounded by the humeral trochlea outer edge 71, the humeral capitulum edge 72, a line L1 drawn from the trochlear axis 73 in the direction of the coronoid fossa, and a line L2 drawn through the trochlear axis 73 in the longitudinal direction of the humerus 76 (in the direction of the ulna 77). Of these, the inner elbow region (the region indicated by the low-density dot in FIG. 2) of the line L3 drawn from the trochlear axis 73 to the end of the radius 75 is the misalignment region in the forearm direction (the first misalignment region), the outer elbow region (the region indicated by the high-density dot in FIG. 2) is the misalignment region (the second misalignment region) in the upper arm direction.

In the embodiment, the first and second misalignments are to be judged based on the misalignment of the humeral trochlea outer edge 71 and humeral capitulum edge 72, but the basis is not limited to this and the first and second misalignments may be judged based on the misalignment from the ideal positioning between the other two parts.

In addition to the above, the learned model M, when a radiographic image or other information is input, may output at least one of the misalignment amount, information for changing the position of the part related to the misalignment, the judgement rank for the degree of misalignment, or the presence/absence of an alert.

<2. Console Details>

Next, the console 2 is described in detail.

Figure 5:
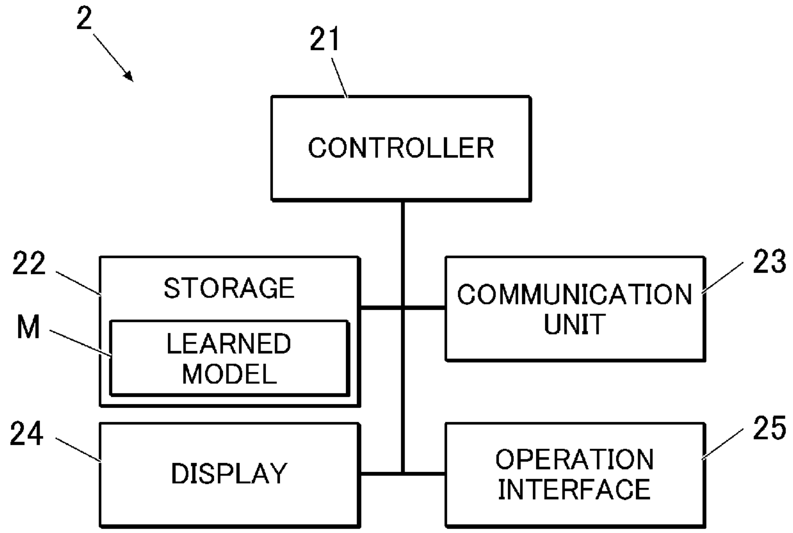
FIG. 5 is a block diagram showing the functional configuration of the console of FIG. 1.
Figure 6:
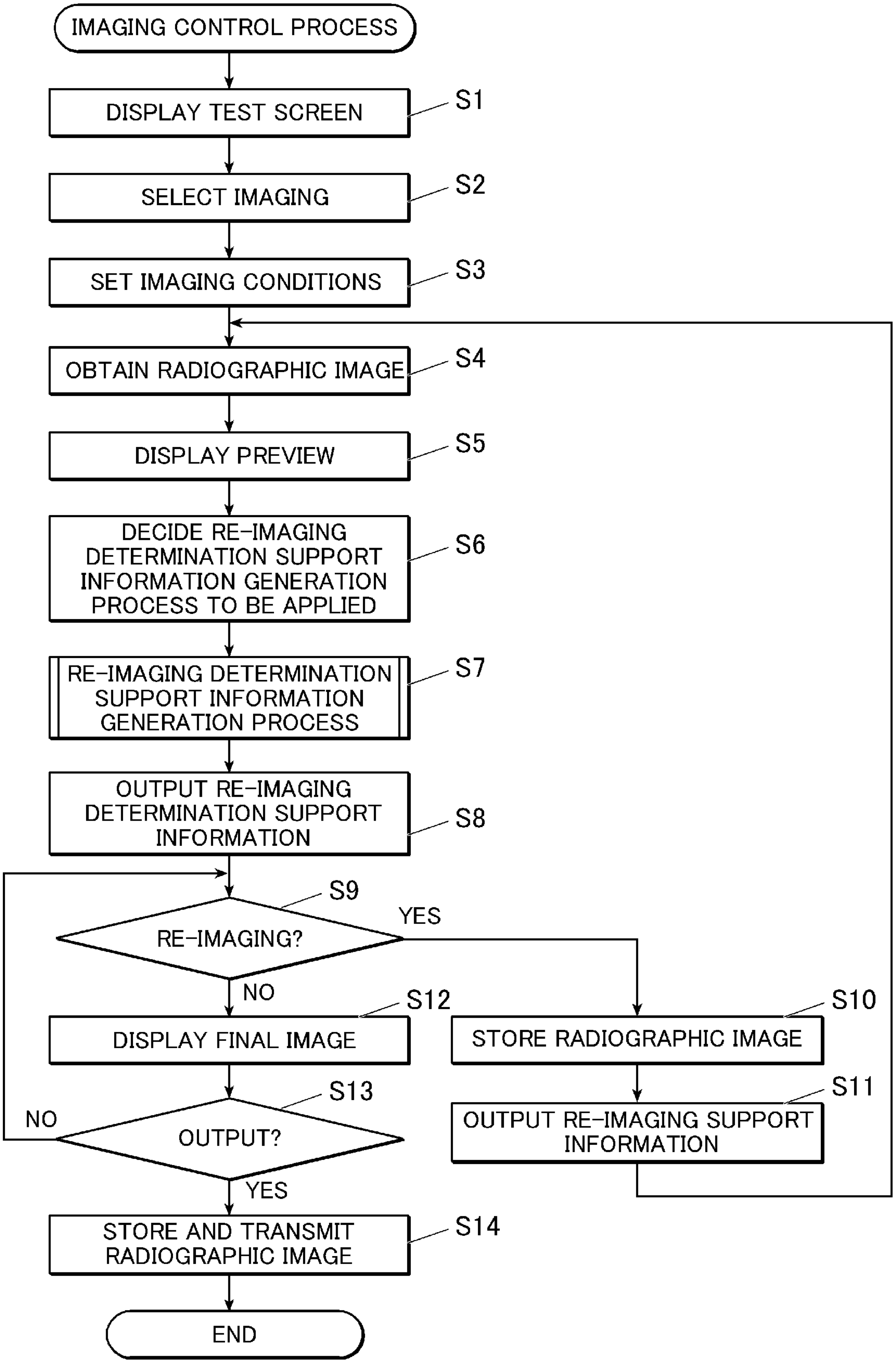
FIG. 6 is a flowchart showing the flow of the imaging control process executed by the controller in FIG. 5.

FIG. 5 is a block diagram showing the functional configuration of the console 2, and FIG. 6 is a flowchart showing the flow of process in the console 2.

[2-1. Console Configuration]

The console 2, as shown in FIG. 5, consists of a controller 21 (hardware processor), a storage 22, a communication unit 23, a the display 24, and an operation interface 25, and each part 21-25 is electrically connected by bus or other means.

The controller 21 consists of a CPU (Central Processing Unit), RAM (Random Access Memory), ROM (Read Only Memory), and the like.

The ROM stores various programs executed by the CPU and parameters necessary for program execution.

The CPU reads various programs stored in ROM and expands them in RAM, executes various processes according to the expanded programs, and centrally controls the operation of each part of the console 2.

By executing the imaging control process described below, the controller 21 functions as the first judging unit, the second judging unit, the outputting unit, and the deciding unit.

The storage 22 consists of a nonvolatile memory, hard disk, and the like.

The storage 22 is capable of storing image data of radiographic images obtained from other devices (the imaging device 1, the image management device 4, and the like).

The storages 22 for the embodiment also stores a plurality of learned models M. The plurality of learned models M include, for example, learned models M generated at the learning device 5.

The storages 22 also stores multiple types of algorithms used in executing the re-imaging determination support information generation process described below.

The storages 22 also stores, so as to be associated with the imaging part and the imaging direction, information (for example, algorithm name) indicating the type of re-imaging determination support information generation process to be performed on the radiographic image for that imaging part and imaging direction, and information (for example, learned model name) indicating the type of learned model M to be used in that process.

The storage 22 also stores test order information sent from RIS and other sources.

The communication unit 23 consists of communication modules and other components.

The communication unit 23 sends and receives various signals and various data to and from other devices (the imaging device 1, generating device 3, the image management device 4, and the learning device 5) connected wirelessly or in a wired manner via communication network N. The communication unit 23 functions as an obtainer.

The display 24 consists of, for example, an LCD (Liquid Crystal Display), CRT (Cathode Ray Tube), or the like. The display 24 displays a radiographic image or other image according to the image signal received from the controller 21.

The operation interface 25 includes a keyboard (cursor keys, numeric input keys, various function keys, and the like), a pointing device (mouse, and the like), and a touch panel layered on the surface of the display 24. The operation interface 25 outputs control signals to the controller 21 in response to operations made by the user.

The console 2 may not include the display 24 and the operation interface 25, but may receive control signals from an input device provided separately from the console 2 via, for example, the communication unit 23, or may output image signals to a display device (monitor) provided separately from the console 2.

If another device (such as the image management device 4) is equipped with a display and operation interface, the control signals may be received from the other device's operation interface or image signals may be output to the other device's display (The display and operation interface may be shared with other devices.)

[2-2. Console Operation]

The operation of the console 2 is described next with reference to FIG. 6.

The console 2 executes the imaging control process shown in FIG. 6. The imaging control process is executed, for example, when test order information is selected by the operation interface 25 from the test list screen displayed on the display 24, in cooperation with the CPU of the controller 21 and the program stored in the ROM.

First, the controller 21 displays test screen 241 on the display 24 for the selected test order information (step S1).

The test screen 241 (see FIG. 7, for example) includes imaging selection buttons 241*a* each of which displays the contents (the imaging part, the imaging direction, and the like) of the imaging included in the test order information, a setting region 241*b* for setting image reading and image processing conditions for the selected imaging, an image display region 241*c* for displaying the imaged radiographic image, an imaging loss button 241*d*, and an output button 241*e*. Note that at the step S1, no radiographic image is yet displayed in the image display region 241*c*. Also, the re-imaging determination support information (indicated by the signs 241*f* to 241*n*), which will be described later, is not displayed.

When the imaging to be performed (the imaging part and the imaging direction) is selected by pressing the imaging selection button 241*a* on the operation interface 25 (step S2), the controller 21 sets the imaging conditions (image reading conditions, radiation irradiation conditions) on the imaging device 1 and the generating device 3 (step S3).

For example, the controller 21 automatically sets imaging conditions (image reading conditions, such as pixel size, image size, frame rate, and the like) for the imaging device 1 based on the imaging part, the imaging direction, and the like of the pressed imaging selection button 241*a*. The controller 21 also sets the imaging conditions (radiation irradiation conditions, for example, tube voltage (kV), tube current (mA), irradiation time (ms), and the like of the radiation source) on the generating device 3. Alternatively, the imaging conditions (image reading conditions) of the imaging to be performed may be set on the imaging device 1 according to the user's operation of the operation interface 25 on the test screen 241. The radiation irradiation conditions may also be set by the user from the operation panel of the generating device 3.

After pressing the imaging selection button 241*a* and setting the imaging conditions, the user (technician) positions the subject S between the radiation source 33 of the generating device 3 and the imaging device 1 to perform positioning. Here, positioning is, for example, how the patient is positioned during imaging.

When the user operates the irradiation instruction switch 32, the generating device 3 emits radiation R to the imaging part of the subject S.

The imaging device 1 generates a radiographic image (still or dynamic image) of the imaging part at the timing of receiving radiation R from the generating device 3, and transmits the image data (still or dynamic image data) to the console 2.

When the image data of the radiographic image is received (obtained) by the communication unit 23 (step S4), the controller 21 performs the preview display of the received radiographic image on the image display region 241*c* of the test screen 241 (step S5).

Next, the controller 21 decides the type of re-imaging determination support information generation process to be applied to the received radiographic image based on the imaging part and the imaging direction of the radiographic image (step S6).

As described above, information indicating the type of re-imaging determination support information generation process to be performed for the radiographic image of the imaging part and the imaging direction is stored in the storage 22 so as to be associated with the imaging part and the imaging direction, and the controller 21 decides the re-imaging determination support information generation process to be applied to the received radiographic image based on the imaging part and the imaging direction of the received radiographic image.

The re-imaging determination support information generation process to be applied to the received radiographic image may be decided when the imaging selection button 241*a* is pressed and the imaging part, the imaging direction, and the like are set. It may also be selected by the user through operation of the operation interface 25, rather than automatically decided by the controller 21.

Next, the controller 21 executes the decided re-imaging determination support information generation process (step S7).

In the re-imaging determination support information generation process, the controller 21 first inputs the received radiographic image to the learned model M corresponding to the imaging part and the imaging direction of the received radiographic image among the multiple learned models M stored in the storage 22, and generates the re-imaging determination support information based on the information output from the learned model M.

The re-imaging determination support information is not limited to information that supports the determination of whether to re-image or not. For example, the re-imaging determination support information includes information about the first misalignment and information about the second misalignment of the predetermined regions in the radiographic image. The information about the misalignment includes, for example, at least one of information about the direction of the misalignment, information about the distance of the misalignment (misalignment amount), information about the misalignment region, a judgement rank for the degree of misalignment, information for changing the position of the part related to the misalignment. The information on the direction of misalignment may include information on the angle of misalignment.

The following is an explanation of the re-imaging determination support information generation process, using the case where the received radiographic image is a radiographic image of the side of the elbow joint as an example.

First, the controller 21 inputs the received radiographic image to the learned model M corresponding to the side of the elbow joint. Once the radiographic image of the side of the elbow joint is input, the learned model M decides the first and second misalignment regions of the input radiographic image based on the imaging part (in this case, the elbow joint), decides the coordinates of the trochlear axis 73, and outputs the information about the first and second misalignment regions (for example, the misalignment region map shown in FIG. 4B, information separating the first and second misalignment regions) and information on the coordinates of the trochlear axis 73. The coordinates of the trochlear axis 73 may be obtained by the controller 21 through image processing.

The controller 21 then generates re-imaging determination support information based on the information output from the learned model M as follows.

First, the controller 21 judges (measures) the misalignment amount in the forearm direction (misalignment amount in the first direction) and the misalignment amount in the upper arm direction (misalignment amount in the second direction) at the elbow joint.

For example, when drawing a straight line in the radial direction from the trochlear axis 73 in the region on the inner side of the elbow than the straight line L3 drawn from the trochlear axis 73 to the end of the radius 75, as shown in FIG. 2, the controller 21 judges the maximum width D1 that intersects perpendicularly to the first misalignment region (the region indicated by the low-density dot in FIG. 2) is judged as the misalignment amount in the forearm direction. In the region outside the elbow than the straight line L3 drawn from the trochlear axis 73 to the end of the radius 75, the maximum width D2 that intersects the second misalignment region (the region indicated by the high-density dot in FIG. 2) perpendicularly when a straight line is drawn from the trochlear axis 73 to the ulna 77 is judged as misalignment amount as the misalignment amount in the upper arm direction.

The misalignment amount may be measured directly, as described above, or indirectly. For example, the misalignment amount in the first direction and the misalignment amount in the second direction may be measured based on the width (for example, maximum width) of the range bounded by the humeral capitulum edge 72 and the humeral trochlea inner edge 78. In this case, a learned model M that uses a radiographic image of the side of the elbow joint as input and outputs the range bounded by the humeral capitulum edge 72 and the humeral trochlea inner edge 78 may be generated by the learning device 5 and stored in the storage 22, or the range to be measured may be obtained by image processing.

The controller 21 then judges the rank of the degree of misalignment (judgement rank) based on the judged misalignment amount and the preset threshold value.

For example, the controller 21 assigns "A rank (good)" when the misalignment amount in the forearm direction is less than threshold TH1 (lowest possibility of imaging failure), "B rank (acceptable)" when it is threshold TH1 or greater and less than threshold TH2, and "C rank (re-imaging)" when it is threshold TH2 or greater (highest possibility of imaging failure). In addition, the controller 21 assigns "A rank (good)" when the misalignment amount in the upper arm direction is less than the threshold value TH11 (lowest possibility of imaging failure), "B rank (acceptable)" when it is the threshold value TH11 or greater and less than the threshold value TH12, and "C rank (re-imaging)" when it is the threshold value TH12 or greater (highest possibility of imaging failure). Then, the lower rank (A rank>B rank>C rank) among the judgement ranks for the forearm direction and the upper arm direction, for example, is used as the overall judgement rank.

If the judgement rank of the misalignment amount in the forearm direction is C, the controller 21 also generates, based on the misalignment amount, information for changing the position of the first part related to the first misalignment (misalignment in the forearm direction) (in this case, for example, the humeral trochlea outer edge 71 or humeral capitulum edge 72). If the judgement rank of the misalignment amount in the upper arm direction is C, then based on the misalignment amount, the controller 21 generates the information for changing the position of the second part (here, the humeral glenoid outer edge 71 or the humeral capitulum edge 72) related to the second misalignment (misalignment in the upper arm direction).

Here, information for changing the position of the part related to the misalignment is information indicating what, in what direction, and how much to move so that the part related to the misalignment is positioned at the correct reference position from its current position on the radiographic image.

For example, information for changing the position of the part related to the misalignment includes information indicating the distance and direction of movement (including the angle of movement) to move the part from its current position to the correct reference position. For example, if the misalignment amount in the upper arm direction is 2 cm, the information for changing the position of the part related to the misalignment would include, for example, notification information such as "When re-imaging, please move the outer edge of the humeral trochlea 2 cm upward".

If there is another object that can be moved from its current position to move the part related to the misalignment from its current position to the correct reference position on the radiographic image, the distance and direction of movement (including the angle of movement) to move the object may be used as the information for changing the position of the part related to the misalignment.

For example, if moving the shoulder position up 2 cm relative to the panel (the imaging device 1) allows the part related to the misalignment to be moved from its current position to the correct reference position, then "When re-imaging, raise the shoulder height relative to the panel (FPD) by 2 cm" or other notification information may be generated as the information for changing the position of the part related to the misalignment. If, for example, the center of irradiation of the radiation source 33 can be turned inward by 5 degrees and rotated outward by 2 degrees to move the part related to the misalignment from its current position to the correct reference position, notification information such as "When re-imaging, please internally turn the center of irradiation 5 degrees and externally rotate 2 degrees" may be generated as the information for changing the position of the part related to the misalignment.

The information for changing the position of the part related to the misalignment can be generated, for example, by experimentally obtaining in advance the relationship between the misalignment direction and misalignment amount of the part related to the misalignment, the target to be moved, the movement distance and the direction of movement of the target to create a table or the like, storing the table or the like in the storage 22, and generating the information for changing the position of the part related to the misalignment according to the table or the like.

Ideally, the misalignment should be zero, but if the misalignment amounts are diagnostically acceptable, the information for changing the position related to the misalignment does not need to be generated.

The controller 21 also creates a misalignment region map by superimposing a predetermined color indicating that it is the misalignment region, on the misalignment region in the radiographic image, and at the position where the misalignment amount was measured, the marker is superimposed.

When the generation of re-imaging determination support information is completed, the controller 21 outputs the generated re-imaging determination support information (step S8).

For example, the controller 21 displays the generated re-imaging determination support information on the display 24 (test screen 241).

Figure 7:
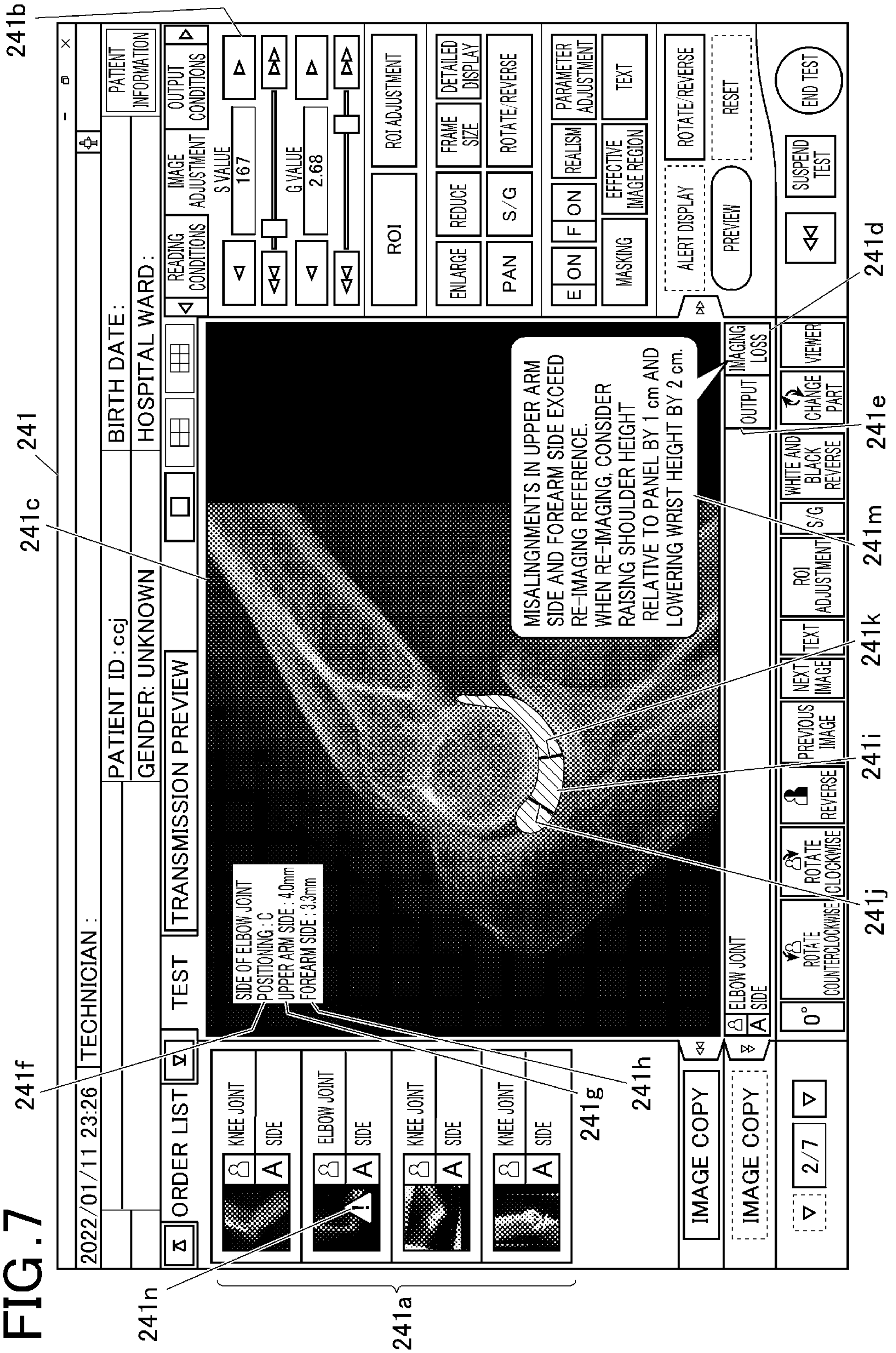
FIG. 7 shows an example display of re-imaging determination support information.

FIG. 7 shows an example of the test screen 241 with a preview image of the radiographic image received from the imaging device 1 and the re-imaging determination support information.

As shown in FIG. 7, in step S8, the received radiographic image is previewed in the image display region 241*c* of the test screen 241. In addition, the re-imaging determination support information is displayed. In FIG. 7, as the re-imaging determination support information, a judgement rank 241*f*, a misalignment amount 241*h* in the first direction, a misalignment amount 241*g* in the second direction, a misalignment region map 241*i*, a measurement position 241*k* of the misalignment amount in the first direction, a measurement position 241*j* of the misalignment amount in the second direction, and "information for changing the position of the part related to the misalignment" (information for changing the position of the first part related to the first misalignment and information for changing the position of the second part related to the second misalignment) 241*m* are displayed. If the judgement rank is C, an alert 241*n* is displayed indicating that re-imaging is necessary.

In addition, only some of the above information may be generated and displayed as re-imaging determination support information, rather than all of the above.

The user (imaging personnel) checks the radiographic image and the re-imaging determination support information, finally determines whether or not re-imaging is necessary, and if he/she determines that re-imaging is necessary, he/she presses the imaging loss button 241*d*. Here, "imaging loss" means that when re-imaging is performed due to imaging failure, the failed image is labeled so that it is not used for diagnosis.

The controller 21 determines whether or not the imaging loss button 241*d* is pressed by the operation interface 25 to instruct re-imaging (step S9).

If it is determined that re-imaging is instructed by pressing the imaging loss button 241*d* on the operation interface 25 (step S9; YES), the controller 21 stores the radiographic image that is determined to require re-imaging in the storage 22, so as to be associated with a flag indicating the imaging loss, a judgement rank, information on the misalignment region and misalignment amount, part information, and information on the technician in charge (step S10).

By accumulating and storing the radiographic images that have been determined to require re-imaging so as to be associated with the judgement rank, information on the misalignment region and misalignment amount, part information, and information on the technician in charge, and the like, it is possible to help educate future imaging personnel.

The controller 21 then outputs the re-imaging support information (step S11).

For example, the controller 21 displays re-imaging support information on the display 24 (test screen 241).

The re-imaging support information is not limited as long as it is information that supports re-imaging. For example, among the information generated as re-imaging determination support information, information for changing the position of the part related to the misalignment is useful re-imaging support information. Information on the direction of misalignment, information on the distance of misalignment (misalignment amount), information on the misalignment region, and the like may also be re-imaging support information. New information that has not been generated as re-imaging determination support information may be generated and output as re-imaging support information.

Figure 8:
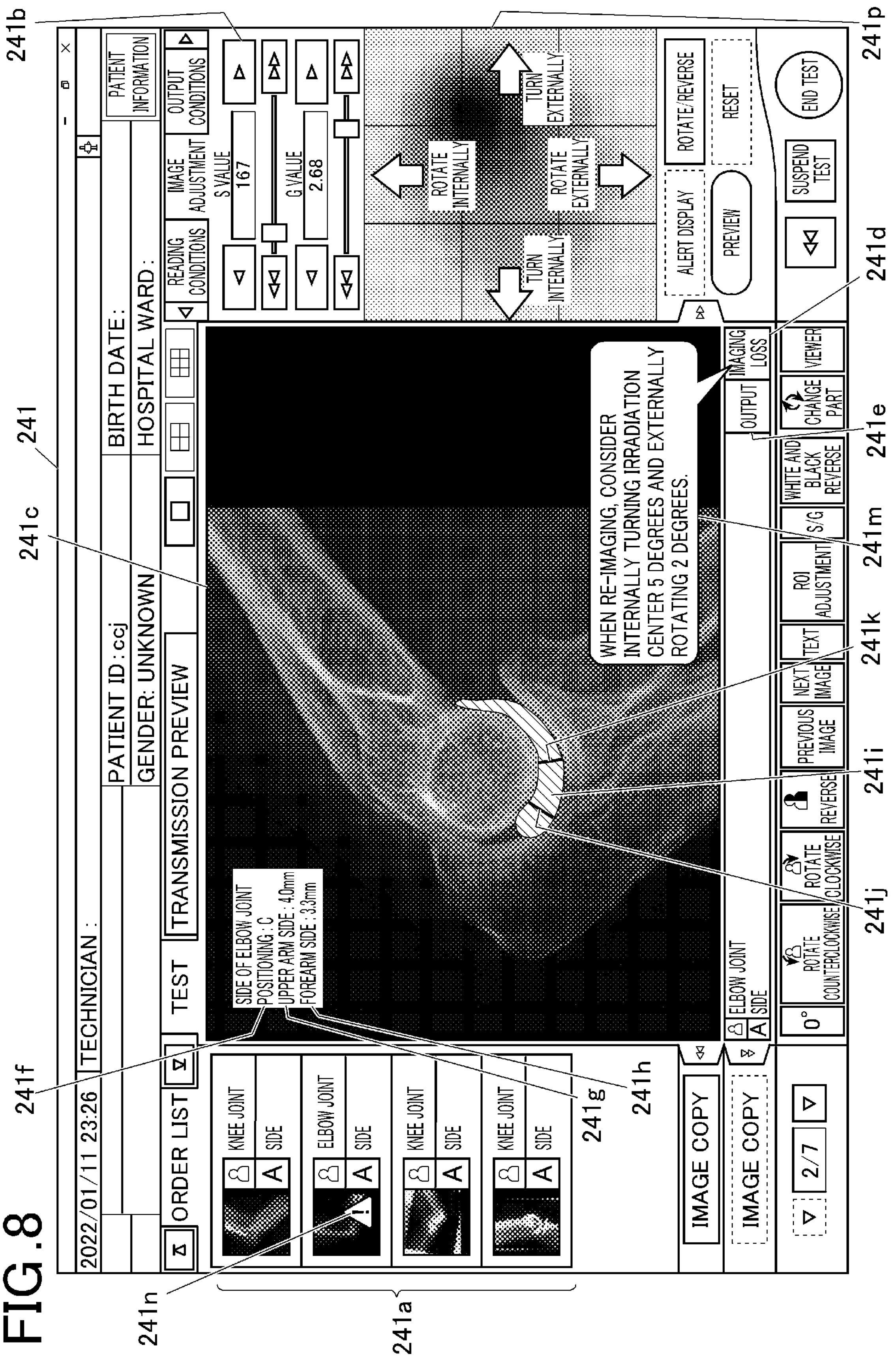
FIG. 8 shows an example display of re-imaging support information.

For example, if the learned model M outputs information indicating the direction of the misalignment from the ideal position of the center of irradiation at the time of imaging (certainty for each direction), as re-imaging support information, as shown in FIG. 8, a heat map 241*p* showing the direction of misalignment of the center of irradiation may be generated and displayed. In the heat map 241*p* shown in FIG. 8, the center of the 9-divided regions is the ideal location of the irradiation center, and the direction of misalignment of the irradiation center output from the learned model M with a higher degree of certainty is indicated in a darker color. FIG. 8 shows that the irradiation center at the time of imaging was about 5 degrees externally turned and 2 degrees internally rotated from the ideal position. Internal/external turn represents rotation in the left/right direction, and internal/external rotation represents rotation in the up/down direction. Along with the heat map 242*p*, information indicating how much the center of irradiation should be shifted in which direction may be displayed as the information for changing the position of the part related to misalignment 241*m*.

The heat map 241*p* may be generated and output as re-imaging determination support information.

The user refers to the displayed radiographic image preview image and re-imaging support information to re-set imaging conditions and perform re-positioning to perform re-imaging.

The controller 21 returns to step S4 (S3) in response to operation of the operation interface 25 or receipt of the radiographic image by the communication unit 23, and repeats steps S4 (S3) to S8.

On the other hand, if it is determined in step S9 that the imaging loss button 241*d* is not pressed by the operation interface 25 (step S9; NO), the controller 21 applies the specified image processing to the radiographic image and displays it as the final image in the image display region 241*c* (step S12).

When image processing conditions, and the like, in the setting region 241*b* are operated by the user, the controller 21 performs image processing according to the operation.

The controller 21 determines whether the output button 241*e* is pressed by the operation interface 25, and if it is determined that the output button 241*e* is not pressed (step S13; NO), the process returns to step S9.

If it is determined that the output button 241*e* is pressed by the operation interface 25 (step S13; YES), the controller 21 associates the radiographic image generated as the final image with a flag indicating that it is not an imaging loss, part information, information on the technician in charge, and the like and stores them in the storage 22. The controller 21 also associates the radiographic image generated as the final image with patient information and test information (test ID, test date, the imaging part, the imaging direction, and the like) and transmits them to the image management device 4 by the communication unit 23 (step S14), and the imaging control process is completed.

As explained above, the controller 21 of the console 2 judges the first misalignment of a predetermined region of a radiographic image, judges the second misalignment of a predetermined region of said radiographic image, and on the basis of at least the judgement of the first misalignment and the judgement of the second misalignment, the controller 21 outputs re-imaging determination support information to assist in determining whether or not the radiographic image should be re-imaged.

Therefore, the misalignment of joint positioning can be judged with high accuracy, and effective re-imaging determination support information can be output.

The controller 21 also outputs information about the first misalignment and information about the second misalignment as re-imaging determination support information.

Thus, it can assist the imaging personnel to easily understand what misalignment is occurring in a predetermined region of a radiographic image.

For example, the controller 21 outputs information for changing the position of the first part related to the first misalignment and information for changing the position of the second part related to the second misalignment as re-imaging determination support information.

Thus, it is possible to assist the imaging personnel to easily understand how to change the position of the first and second parts to achieve the correct positioning.

For example, the controller 21 outputs the movement distance of the first part as information for changing the position of the first part and the movement distance of the second part as information for changing the position of the second part.

Thus, it is possible to assist the imaging personnel to easily understand how much to move the position of the first part and the second part to achieve the correct positioning.

For example, the controller 21 outputs the movement direction of the first part as information for changing the position of the first part, and the movement direction of the second part as information for changing the position of the second part.

Thus, it is possible to assist the imaging personnel to easily understand in which direction the first and second parts should be moved to achieve the correct positioning.

For example, the controller 21 outputs re-imaging determination support information along with information indicating that re-imaging is necessary.

Thus, it is possible to assist the imaging personnel to easily determine whether or not re-imaging is necessary.

The controller 21 also judges the first misalignment of the predetermined region of the radiographic image, judges the second misalignment of the predetermined region of the radiographic image, and based on at least the judgement of the first misalignment and the judgement of the second misalignment, the controller 21 outputs re-imaging support information to assist in the re-imaging of the radiographic image.

Therefore, the misalignment of joint positioning can be judged with high accuracy, and effective re-imaging support information can be output.

In addition, the console 2 has a learned model M, in which at least a radiographic image, information about the first misalignment of a predetermined region of the radiographic image, and information about the second misalignment of a predetermined region of the radiographic image, are learned as teacher data. The controller 21 outputs the determination support information that supports the determination whether or not to re-image the radiographic image based on the learned model M and the obtained radiographic image.

Therefore, the misalignment of joint positioning can be judged with high accuracy, and effective re-imaging determination support information can be output.

The learning device 5 also learns at least the radiographic image, information about the first misalignment of the predetermined region of the radiographic image, and information about the second misalignment of the predetermined region of the radiographic image, as teacher data to generate a learned model. Thus, a learned model can be generated that outputs information about the first misalignment and information about the second misalignment from the input radiographic image.

The present invention is not limited to the above embodiments or the like, but can be modified as appropriate to the extent not to depart from the scope of the present invention.

For example, in the above embodiment, the case of applying the present invention to re-imaging determination support and re-imaging support in imaging radiographic images of the side of the elbow joint is described as an example, but the present invention can be applied to re-imaging determination support and re-imaging support in imaging radiographic images of other joints such as the knee joint and ankle joint, for example.

In the above embodiment, the misalignment regions were described as being extracted from a radiographic image using machine learning, but the misalignment regions may also be extracted by image processing.

In addition to misalignment regions, re-imaging determination support information and re-imaging support information may also be generated by machine learning.

In the above embodiment, the case in which the functions of the re-imaging determination support device and the re-imaging support device of the present invention are mounted on the console 2 is described as an example, but the functions of the re-imaging determination support device and the re-imaging support device may be mounted on a device different from the console 2 or may be a dedicated device. The functions of the learning device 5 may be performed by the console 2.

In the above embodiment, the controller 21 of the console 2 is described as displaying the re-imaging determination support information and re-imaging support information on the display 24, but it may also be displayed on a display device that is separate from the console 2.

The re-imaging determination support information and re-imaging support information may be not only displayed, but may be output as audio by an audio output device not shown in the figure.

The controller 21 of the console 2 may also output the results of the misalignment judgement (information about misalignment), the radiographic image used for judgement of misalignment (generation of information about misalignment), threshold information, algorithm type, and other contents to an external device so that they can be confirmed on the external device. In addition, the misalignment judgement function (for example, the program for executing the re-imaging determination support information generation process described above or the learned model M used) itself may be output to an external device so that the misalignment judgement can be performed at the external device.

For example, the above description discloses an example using a hard disk, semiconductor nonvolatile memory, or the like as a computer-readable medium for the program in the present invention, but it is not limited to this example. As other computer readable media, portable recording mediums such as CD-ROMs can be applied. Carrier wave (carrier wave) is also applicable as a medium for providing data of the program for the present invention via communication lines.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A re-imaging determination support device comprising a hardware processor that:

judges a first misalignment in a first direction of a first region of a predetermined region in a radiographic image;

judges a second misalignment in a second direction of a second region of the predetermined region in the radiographic image;

outputs re-imaging determination support information that supports determining whether or not to perform re-imaging for the radiographic image, based on at least a judgement of the first misalignment in the first direction and a judgement of the second misalignment in the second direction; and outputs information indicating the first misalignment in the first direction and the second misalignment in the second direction from an ideal position of the predetermined region, wherein the first region and the second region are in a same joint region.

2. The re-imaging determination support device according to claim 1, wherein the hardware processor judges a misalignment amount in the first direction of the first region of the predetermined region in the radiographic image as the judgement of the first misalignment, judges a misalignment amount in the second direction of the second region of the predetermined region in the radiographic image as the judgement of the second misalignment, and outputs the re-imaging determination support information based on a judgement of the misalignment amount in the first direction and a judgement of the misalignment amount in the second direction.

3. The re-imaging determination support device according to claim 2, wherein the hardware processor outputs information for changing a position of a first part related to the first misalignment based on the misalignment amount in the first direction and outputs information for changing a position of a second part related to the second misalignment based on the misalignment amount in the second direction, as the re-imaging determination support information.

4. The re-imaging determination support device according to claim 1, wherein the hardware processor outputs information about the first misalignment and information about the second misalignment as the re-imaging determination support information.

5. The re-imaging determination support device according to claim 1, wherein the hardware processor outputs information for changing a position of a first part related to the first misalignment and information for changing a position of a second part related to the second misalignment, as the re-imaging determination support information.

6. The re-imaging determination support device according to claim 5, wherein the hardware processor outputs a movement distance of the first part as the information for changing the position of the first part and outputs a movement distance of the second part as the information for changing the position of the second part.

7. The re-imaging determination support device according to claim 5, wherein the hardware processor outputs a movement direction of the first part as the information for changing the position of the first part and outputs a movement direction of the second part as the information for changing the position of the second part.

8. The re-imaging determination support device according to claim 1, wherein the hardware processor outputs the re-imaging determination support information along with information indicating that re-imaging is necessary.

9. The re-imaging determination support device according to claim 1, wherein the hardware processor decides the predetermined region based on imaging part information.

10. The re-imaging determination support device according to claim 1, wherein the first region of the predetermined region for which the first misalignment is judged includes an amount of a range bounded by a humeral trochlea outer edge and a humeral capitulum edge in a forearm direction, and the second region of the predetermined region for which the second misalignment is judged includes an amount of a range bounded by the humeral capitulum edge and a humeral trochlea inner edge in an upper arm direction, in a side of an elbow joint.

11. The re-imaging determination support device according to claim 1, wherein the predetermined region is a joint of a subject.

12. A learning device comprising a hardware processor that:

learns with at least a radiographic image, information about a first misalignment in a first direction of a first region of a predetermined region in the radiographic image, and information about a second misalignment in a second direction of a second region of the predetermined region in the radiographic image, as teacher data, generates a learned model which determines re-imaging determination support information that supports determining whether or not to perform re-imaging for the radiographic image, based on the first misalignment and the second misalignment; and generates a learned model which estimates the information about the first misalignment and the information about the second misalignment of the predetermined region from the input radiographic image, wherein the first region and the second region are in a same joint region.

13. A re-imaging determination support device comprising:

a learned model in which at least a radiographic image, information about a first misalignment in a first direction of a first region of a predetermined region in the radiographic image, and information about a second misalignment in a second direction of a second region of the predetermined region in the radiographic image are learned as teacher data;

an obtainer that obtains a radiographic image;

a hardware processor that outputs re-imaging determination support information that supports determining whether or not to perform re-imaging for the radiographic image, based on the learned model and the radiographic image obtained by the obtainer, outputs information indicating the first misalignment in the first direction and the second misalignment in the second direction from an ideal position of the predetermined region, wherein the first region and the second region are in a same joint region.

14. A re-imaging support device comprising a hardware processor that:

judges a first misalignment in a first direction of a first region of a predetermined region in a radiographic image;

judges a second misalignment in a second direction of a second region of the predetermined region in the radiographic image; and outputs re-imaging support information that supports re-imaging for the radiographic image, based on at least a judgement of the first misalignment in the first direction and a judgement of the second misalignment in the second direction; and outputs information indicating the first misalignment in the first direction and the second misalignment in the second direction from an ideal position of the predetermined region, wherein the first region and the second region are in a same joint region.

15. A non-transitory recording medium storing a computer-readable program, the program causing a computer to perform:

first judging that is judging a first misalignment in a first direction of a first region of a predetermined region from a radiographic image;

second judging that is judging a second misalignment in a second direction of a second region of the predetermined region in the radiographic image;

outputting that is outputting re-imaging determination support information that supports determining whether or not to perform re-imaging for the radiographic image, based on at least a judgement of the first misalignment in the first direction and a judgement of the second misalignment in the second direction; and outputs information indicating the first misalignment in the first direction and the second misalignment in the second direction from an ideal position of the predetermined region, wherein the first region and the second region are in a same joint region.

16. The recording medium according to claim 15, wherein the program causes the computer to judge a misalignment amount in the first direction of the first region of the predetermined region in the radiographic image as the judgement of the first misalignment in the first judging, judge a misalignment amount in the second direction of the second region of the predetermined region in the radiographic image as the judgement of the second misalignment in the second judging, and output the re-imaging determination support information based on a judgement of the misalignment amount in the first direction and a judgement of the misalignment amount in the second direction in the outputting.

17. The recording medium according to claim 16, wherein the program causes the computer to output information for changing a position of a first part related to the first misalignment based on the misalignment amount in the first direction and output information for changing a position of a second part related to the second misalignment based on the misalignment amount in the second direction, as the re-imaging determination support information, in the outputting.

18. The recording medium according to claim 15, wherein the program causes the computer to output information about the first misalignment and information about the second misalignment as the re-imaging determination support information in the outputting.

19. The recording medium according to claim 15, wherein the program causes the computer to output information for changing a position of a first part related to the first misalignment and information for changing a position of a second part related to the second misalignment, as the re-imaging determination support information, in the outputting.

20. The recording medium according to claim 19, wherein the program causes the computer to output a movement distance of the first part as the information for changing the position of the first part and output a movement distance of the second part as the information for changing the position of the second part, in the outputting.

21. The recording medium according to claim 19, wherein the program causes the computer to output a movement direction of the first part as the information for changing the position of the first part and output a movement direction of the second part as the information for changing the position of the second part, in the outputting.

22. The recording medium according to claim 15, wherein the program causes the computer to output the re-imaging determination support information along with information indicating that re-imaging is necessary, in the outputting.

23. The recording medium according to claim 15, wherein the program causes the computer to perform deciding that is deciding the predetermined region based on imaging part information.

24. The recording medium according to claim 15, wherein the predetermined region for which the first misalignment is judged and the predetermined region for which the second misalignment is judged include a range bounded by a humeral trochlea outer edge and a humeral capitulum edge, or by the humeral capitulum edge and a humeral trochlea inner edge, in a side of an elbow joint.

25. A re-imaging determination support method comprising:

first judging that is judging a first misalignment in a first direction of a first region of a predetermined region in a radiographic image;

second judging that is judging a second misalignment in a second direction of a second region of the predetermined region in the radiographic image;

outputting that is outputting re-imaging determination support information that supports determining whether or not to perform re-imaging for the radiographic image, based on at least a judgement of the first misalignment in the first direction and a judgement of the second misalignment in the second direction; and outputs information indicating the first misalignment in the first direction and the second misalignment in the second direction from an ideal position of the predetermined region, wherein the first region and the second region are in a same joint region.

* * * * *